(12) United States Patent
Litzke et al.

(10) Patent No.: US 8,676,321 B2
(45) Date of Patent: Mar. 18, 2014

(54) CONNECTION HOUSING AND MANUFACTURE OF SAME

(75) Inventors: Jan Litzke, Berlin (DE); Joerg John von Freyend, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 143 days.

(21) Appl. No.: 12/958,527

(22) Filed: Dec. 2, 2010

(65) Prior Publication Data

US 2011/0137414 A1    Jun. 9, 2011

Related U.S. Application Data

(60) Provisional application No. 61/266,172, filed on Dec. 3, 2009.

(51) Int. Cl.
*A61N 1/375* (2006.01)

(52) U.S. Cl.
USPC .......................................................... 607/37

(58) Field of Classification Search
None
See application file for complete search history.

(56) References Cited

U.S. PATENT DOCUMENTS

| | | |
|---|---|---|
| 5,620,476 A | 4/1997 | Truex et al. |
| 6,192,277 B1 | 2/2001 | Lim et al. |
| 2001/0034543 A1 | 10/2001 | Haeg et al. |
| 2007/0100385 A1 * | 5/2007 | Rawat et al. ..................... 607/37 |
| 2007/0111587 A1 | 5/2007 | Ries et al. |
| 2007/0255332 A1 | 11/2007 | Cabelka et al. |
| 2007/0270007 A1 * | 11/2007 | Mueller et al. ................ 439/188 |
| 2008/0114413 A1 * | 5/2008 | Fischbach et al. .............. 607/36 |

FOREIGN PATENT DOCUMENTS

WO    01/99239 A2    12/2001

* cited by examiner

*Primary Examiner* — Brian T Gedeon
*Assistant Examiner* — Ankit Tejani
(74) *Attorney, Agent, or Firm* — Buchanan Ingersoll & Rooney PC (57) ABSTRACT

A medical implant includes a hermetically sealed hollow housing having a hermetically sealed feedthrough suitable for conducting electrical signals to and from the hollow housing without impairing the hermetic seal thereof. The hollow housing includes a circuit suitable for measuring signals from the human body, sending signals to the human body, and transmitting signals to a receiver located outside the body. The implant also includes a connection housing having an insulating connection body, an externally accessible cavity for connecting an implantable electrode line, an insulating substrate having at least one electrically conductive strip conductor structure, and contacts that are securely electrically connected to a strip conductor structure present in or on the substrate material. The substrate may be embedded in the connection body in such a way that the contacts are present in the externally accessible cavity.

13 Claims, 5 Drawing Sheets

CONNECTION HOUSING AND MANUFACTURE OF SAME

RELATED APPLICATION

This patent application claims the benefit of U.S. Provisional Patent Application No. 61/266,172, filed on Dec. 3, 2009, which is hereby incorporated by reference in its entirety.

TECHNICAL FIELD

The present patent application relates to a connection housing, or header, for a medical implant, a method for manufacturing same, and a medical implant having such a connection housing.

BACKGROUND

A connection housing (also referred to as a header) is necessary for connecting electrode lines to electrical components of a medical implant. Such a connection housing is generally composed of a connection body made of insulating, preferably transparent, material, which may be a plastic material which preferably includes the materials polyurethane (PU), polycarbonate (PC), and/or epoxy resin. In this connection body at least one externally accessible cavity, in each case containing contacts, is provided for accommodating standard plug-in connectors (such as IS-1, DF-1, or IS-4) for the electrode lines. These electrode lines may be cardiac electrode lines, which may be implanted intracardially or in the form of a coronary sinus (CS) electrode, or nerve or epicardial electrode lines. Such electrode lines may also have another form and function.

The contacts in the cavities are designed as elastic sleeves or plug-in connector receptacles in which the plug-in connector of the electrode line may be inserted, and whose shape and location correspond to that of the standard plug-in connectors. If the connection housing is transparent it can be seen from the outside whether an electrode line plug is inserted far enough into the elastic sleeve or into the plug-in connector receptacle of a particular electrical connection.

The electrical contacts are each connected to one or more electrical conductors which are provided for transmitting electrical signals to these electrical contacts so that the signals may be sent via the electrode line plug to the corresponding electrode at the distal end of the electrode line, and thus to the treatment site in the human or animal body. Electrical signals measured in the body may also be sent in the opposite direction in the same manner. It is known from the prior art that these electrical conductors are composed of an electrically conductive metal, preferably metal wires or metal ribbons. The latter are either formed during installation or punched from a preformed sheet metal strip (in blanks) and connected to the electrical contacts using joining processes such as welding, soldering, or crimping. Such a known approach is described in International Patent Application No. WO 01/99239 A2, the disclosure of which is incorporated in its entirety into the present patent application.

The connection housing may include a base body and/or a connection body which are connected to one another in a suitable manner. Any other design known from the prior art is also possible, in particular a multipart design in which the constituent components are individually joined together. Therefore, in the discussion below reference is made only to a connection housing.

The invention further relates to a medical implant, for example an implantable cardiac pacemaker, defibrillator, cardioverter, nerve stimulator, or the like. The medical implant includes a connection body or header, described at the outset, which is fastened to a hollow housing. The hollow housing is hermetically sealed with respect to the surroundings, and is generally made of biocompatible metal. The hollow housing is used to accommodate an electrical circuit or control electronics system composed, among other things, of capacitors, batteries, and other electrical circuitry. The circuit is provided for measuring signals from the human body, sending signals to the human body, or combinations thereof, and it is also suited for transmitting signals to a receiver located outside the body.

The electrical connection of the electrical circuit in the hollow housing to the electrical conductors present in the header, which are electrically connected to the electrical contacts, is generally achieved via filtered or unfiltered hermetically sealed feedthroughs, also known as glass/ceramic housing feedthroughs. Such feedthroughs are known from the prior art, for example from DE 103 29 261 A1, EP 1 148 910 A1, or EP 1 897 589 A2, the disclosures of which are incorporated in their entirety into the present patent application. The feedthroughs are composed of at least one feedthrough pin, and are embedded in a wall of the hollow housing so as to close off the hollow housing with a hermetically tight seal. The feedthroughs may also be implemented as filter feedthroughs in which the filter has an electrical low-pass filtering effect.

Great demands are placed on the quality of a housing for a medical implant. In particular, the hollow housing and the connection housing must interact reliably and remain tightly sealed for years. The connection housing itself must be stable over a long period of time and have a precise fit.

Various approaches are known from the prior art for meeting the requirements described above. For instance, it is known to integrally cast the connection housing directly onto the hollow housing. For this purpose the hollow housing having conductors for the electrical connections which are attached to the feedthrough pins, using a joining process, and the electrical contacts are inserted into a casting mold, and are cast by filling the closed casting mold with liquid plastic. The liquid plastic is allowed to harden in the casting mold, and after removal of the casting mold results in a connection housing which is produced in a single work step and is directly and securely joined to the hollow housing. Another approach known from patent applications EP 1 795 225 A1 or EP 1 795 226 A1 provides for separate manufacture of the connection housing by first casting same as described above in a casting mold together with the electrical conductors and the electrical contacts, and then electrically connecting the leads to the feedthrough pins for the feedthroughs in the hollow housing a joining process. In addition, the connection housing is glued to the hollow housing a suitable liquid or paste adhesive. The disclosures of the two cited patent applications EP 1 795 225 A1 and EP 1 795 226 A1 are hereby incorporated in their entirety into the present patent application.

The feedthrough pins and the electrical contacts are electrically connected to the electrical conductor before the casting operation by use of a joining process. Such a joining process may include a laser welded connection, welding by means other than a laser, soldering, or gluing using an electrically conductive adhesive, wherein this listing is not to be construed as exhaustive.

The manufacture of a connection housing of the type described above is not without risks. For example, defects may result from the primarily manual production of the connection housing. Although the electrical conductors (ribbons or bent-punched parts) may be fabricated with pre-bending in three dimensions, the further processing is not possible by automated means. Thus, the electrical conductors and the contacts must be welded or soldered by hand and then cast. This results in inadvertent errors, for example in the electrical contacting of the contacts to the conductor.

Furthermore, quality and functional control of the connection housing is not possible until after the connection housing has been completely manufactured. Thus, if minor defects are present the entire connection housing may be unusable. Therefore, there is a need for a connection housing or a medical implant which can be manufactured by automated means and which may be easily tested for quality and functionality before final manufacture without complete installation being necessary.

SUMMARY

One embodiment of the invention comprises an improved connection housing for a medical implant having a connection body made of electrically insulating material which has at least one externally accessible cavity for connecting an implantable electrode line, and a substrate made of insulating material to which is mounted at least one electrically conductive strip conductor structure, wherein one or more contacts are securely electrically connected to one or more of the strip conductor structure present on the substrate material of the substrate, and the substrate is at least partly embedded in the connection body in such a way that the contacts are present in the externally accessible cavity.

Within the meaning of the present disclosure, a substrate is implemented as a circuit board (also known as a printed circuit board (PCB), printed circuit, or conductor board), to which may be attached electronic components such as resistors, coils, capacitors, and the like. The circuit board is used for both mechanical attachment and electrical connection. The substrate is normally composed of an insulating, non-transparent material which is typically fiber-reinforced plastic, ceramic, or flame-retardant substrates made of paper such as FR1/FR2 substrates (phenol resin and paper) or FR3 substrates (epoxy resin and paper), flame-retardant substrates made of fiberglass fabric such as FR4/FR5 substrates (epoxy resin and fiberglass fabric), BT substrate, CE substrate, epoxy resin laminates such as CEM1 or CEM3 substrates, PD substrates, polytetrafluoroethylene (PTFE) substrates, CHn substrates, polyimide films (Kapton films), polyester, or high-density interconnect (HDI) conductor boards. The substrate also includes conductive connections (e.g., strip conductor structures) located on or in the substrate material preferably made of an electrically conductive material such as copper, aluminum, gold, silver, stainless steel, titanium, niobium, tantalum, or conductive adhesives or plastics. The strip conductor structures themselves may be punched or etched from a thin layer of the materials mentioned immediately above, and the punched or etched strip conductor structures may be glued to the substrate. The electronic components are soldered onto soldering surfaces such as pads or soldering lands. The components are thus simultaneously mechanically held and electrically connected. It is further noted that the strip conductor structures may have a wire or ribbon shape.

This system allows internal wiring within the connection housing to be pre-assembled. In other words, by use of a suitable design the substrate may be fabricated before the connection housing is assembled, and in this state may also be tested before installation or casting of the complete connection housing. This reduces the cost of materials and increases the reliability of the connection housing.

According to a further embodiment, a method is provided for manufacturing a connection housing for a medical implant made of electrically insulating material which has at least one externally accessible cavity for connecting an implantable electrode line, and a substrate made of insulating material having at least one electrically conductive strip conductor structure. One or more contacts are securely electrically connected to one or more of the strip conductor structure present on the substrate material of the substrate, and the substrate is embedded in the connection body in such a way that the contacts are present in the externally accessible cavity. The method comprises the following steps:

Placing an electrical substrate having contacts securely electrically connected thereto in an injection mold, Carrying out an extrusion/extrusion coating operation for the connection body in such a way that the substrate is embedded in the connection body by extrusion coating or casting so that the contacts are present in the externally accessible cavity.

The method may further comprise an additional method step between the placement step and the extrusion/extrusion coating operation, wherein a passivation or insulation layer which is different from the connection body material may be applied directly to the substrate. The passivation or insulation layer may be, for example, a high-voltage insulating coating between the connection housing and the substrate. This passivation or insulation layer may be composed of organic or inorganic materials and mixtures thereof (for example, ceramics or polymers).

In this manner the entire manufacturing process may be optimized and accelerated, since because the connection housing and the medical implant are assembled with fewer production steps. The acceleration is achieved primarily due to the fact that the pre-assembled and tested substrate is provided for the assembly process for the connection housing and the medical implant. Extensive wiring and testing during final assembly may thus be avoided.

A further embodiment of the invention concerns a medical implant comprising the following:

a hollow housing which is hermetically sealed and has at least one hermetically sealed feedthrough which is suitable for conducting electrical signals through the hollow housing without impairing the hermetic seal thereof, the hermetically sealed feedthrough having at least one feedthrough pin, a circuit present in the hollow housing, the circuit being suitable for measuring signals from the human body and sending signals to the human body, and being suitable for transmitting signals to a receiver located outside the body, and a connection housing which is securely joined to the hollow housing and has a connection body made of electrically insulating material and having an externally accessible cavity for connecting an implantable electrode line, and a substrate composed of insulating material and having at least one electrically conductive strip conductor structure, and one or more contacts which are securely electrically connected to one or more of the strip conductor structure located in or on the substrate material of the substrate, the substrate being embedded in the connection body in such a way that the contacts are present in the externally accessible cavity.

In this manner each feedthrough pin of the feedthrough in the hollow housing is electrically connected to a different one of the electrically conductive strip conductor structures of the connection housing.

Further advantages or aspects of the connection housing according to the invention, the manufacturing method, or the medical implant will become apparent from the following drawings and the description of the drawings.

DETAILED DESCRIPTION

Figure 1A:
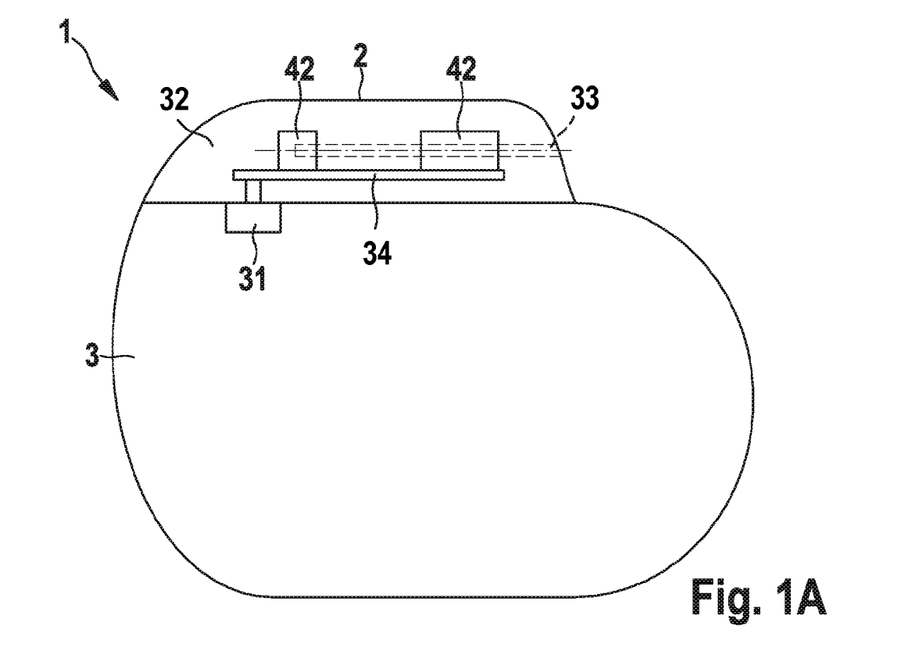
FIG. 1A shows a medical implant according to a first embodiment.
Figure 1B:
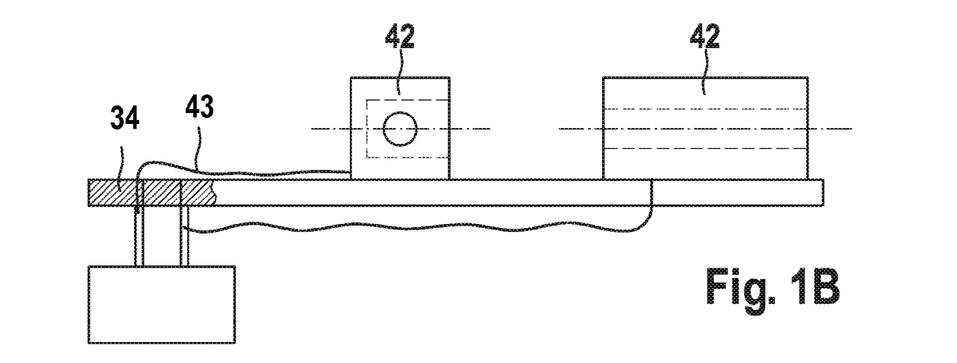
FIG. 1B shows a side elevation view of a substrate assembly for a medical implant according to the first embodiment.
Figure 1C:
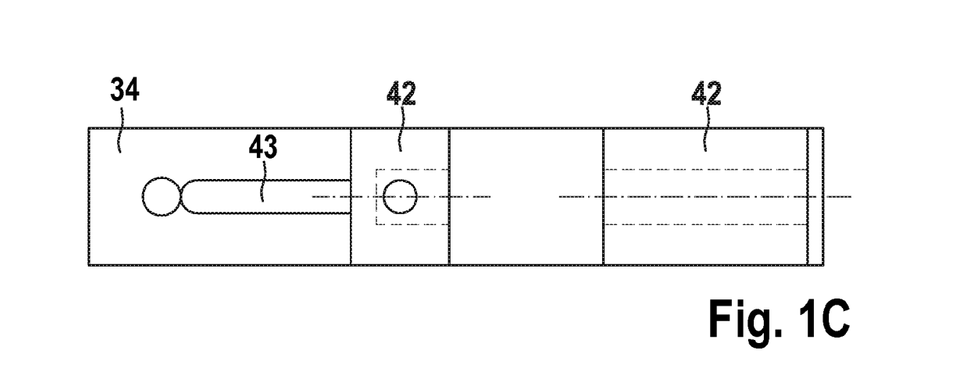
FIG. 1C shows a top view of the substrate assembly shown in FIG. 1B.

FIGS. 1A-1C show a medical implant 1 according to a first embodiment, having an improved connection housing 2 and a hollow housing 3. The hollow housing 3 is hermetically sealed, and is generally made of a biocompatible metal such as titanium. The hollow housing also has at least one hermetically sealed feedthrough 31, embedded on or in the hollow housing 3, which is suitable for conducting electrical signals through the hollow housing 3 without impairing the hermetic seal thereof. The hermetically sealed feedthrough 31 has at least one feedthrough pin.

The hollow housing 3 may be used to accommodate a circuit or control electronics system composed, among other things, of capacitors, batteries, and other electrical circuitry. The circuit is preferably suited for measuring signals from the human body and sending signals to the human body, and is also suited for transmitting signals to a receiver located outside the body.

The connection housing 2 includes a connection body 32 made of electrically insulating, preferably transparent, material, which may be a plastic material which preferably includes the materials polyurethane (PU), polycarbonate (PC), or epoxy resin or combinations thereof. The connection housing 2 also includes at least one externally accessible cavity 33 in the connection body 32 for connecting an implantable electrode line (not illustrated), and a substrate 34 made of insulating material and likewise embedded in the connection body 32 and having at least one electrically conductive strip conductor structure 43. One or more electrical contacts 42 are securely electrically connected to one or more conductor structures 43 located in or on the substrate material of the substrate 34, and the substrate 34 is embedded in the connection body 32 in such a way that the contacts are present in the externally accessible cavity, whereas the remainder of the substrate is surrounded by the insulating material of the connection body 32. The electrical contacts 42 are electrically connected to the strip conductor structure(s) 43 by use of a joining process. Such a joining process includes forming a connection using a laser beam, welding, soldering, or gluing using an electrically conductive adhesive, wherein this listing is not to be construed as exhaustive.

Figure 2A:
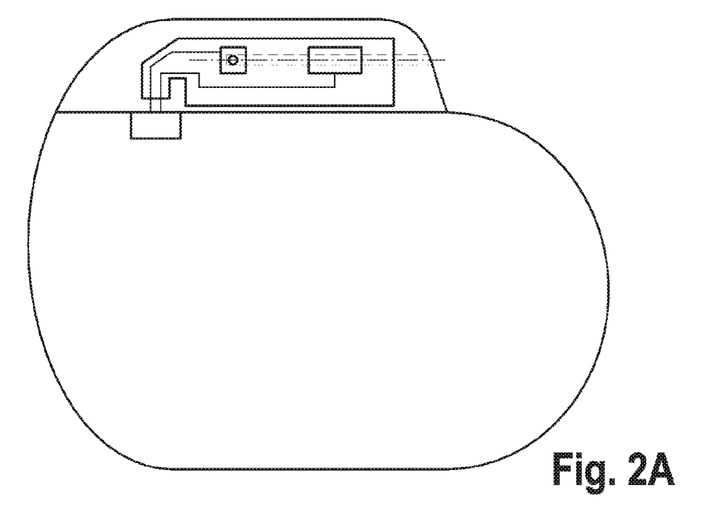
FIG. 2A shows a medical implant according to a second embodiment in which the substrate lies in a common plane with the hollow body.
Figure 2B:
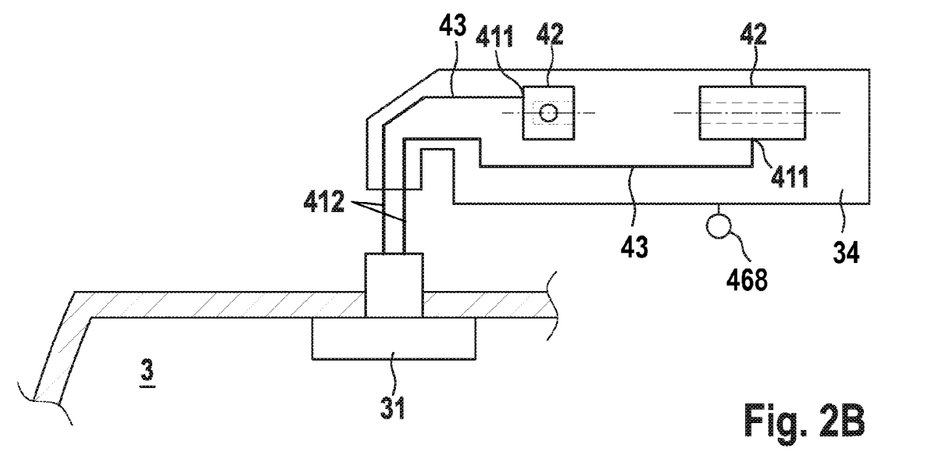
FIG. 2B shows a detailed view of the substrate according to the second embodiment, with a connection to the hollow body.

FIGS. 2A and 2B show in detailed views the substrate 34 according to a second embodiment in which one or more of the strip conductor structures 43 of the connection housing 2 have a first end 411 to which the contacts 42 are securely electrically connected, and a second end 412. Each of the two ends 411 and 412 of the strip conductor structures 43 is electrically connected to a feedthrough pin. The feedthrough pins for the feedthrough 31 and the strip conductor structure 43 are then soldered, welded, glued, or joined together, thus forming an electrical connection.

The contacts 42 preferably include plug-in connector receptacles or elastic sleeves known from the prior art. However, the contacts 42 may also have other suitable shapes for accommodating a plug-in connector, which may become necessary, for example, when new plug-in connector standards such as IS-4 are introduced.

The connection housing 2, or the substrate 34, or both preferably may also have additional anchoring possibilities to improve the attachment of the connection housing 2 to the is hollow housing 3.

Figure 3A:
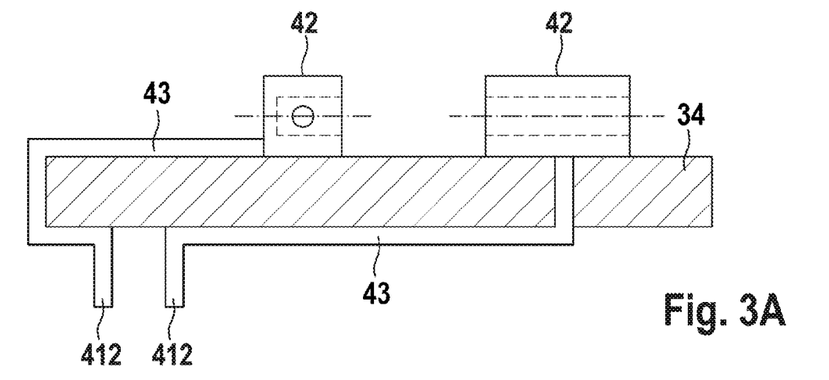
FIGS. 3A and 3B show sectional views of a substrate for the connection housing of a medical implant, showing various strip conductor structures.

The substrate 34 is described in greater detail below. FIG. 3A shows a sectional view of the substrate 34, which is designed as a printed circuit board (PCB) (printed circuit or conductor board). The strip conductor structure 43 for the substrate material is mounted on the substrate 34, or preferably is embedded in the substrate 34 in such a way that a strip conductor surface facing away from the substrate 34 is not covered by the substrate material. In the first case the strip conductor structure 43 has a so-called outer wiring in which the strip conductor structures 43 rest on the substrate. The substrate is used only to mechanically fasten the contacts 42, for example by gluing. The electrical connection is established via the strip conductor structures 43 resting on the substrate 34. The contacts 42 may also optionally be electrically connected to the feedthrough 31 for the hollow housing 3 by means of a bonding wire in the form of a strip conductor structure 43.

Figure 3B:
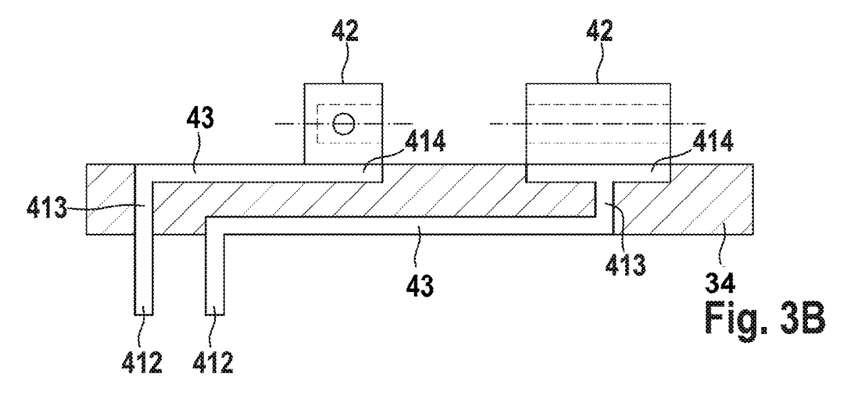

In the second case illustrated in FIG. 3B as a sectional illustration of a substrate 34, conventional one- or two-layer printed conductor boards are used in which strip conductor structures 43 are cleared from the insulating substrate material using an etching process. Vias provide the required electrical connections through the substrate. The strip conductor structures 43 are thus embedded in substrate 34 without insulation on one side, and are securely connected to the substrate material. In this implementation, both a mechanical and an electrical connection to the substrate 34 are present, because the electrical contacts 42 are electrically and mechanically connected on soldering pads 414, or lugs, using the referenced joining process. This embodiment is particularly suitable for automated pre-assembly of the substrates 34 using surface-mounted device (SMD) techniques.

According to a preferred embodiment, the substrate 34 for the connection housing 2 is made of a rigid material such as, for example, fiber-reinforced plastic, ceramic, flame-retardant paper such as FR1/FR2 (phenol resin and paper) or FR3 (epoxy resin and paper); flame-retardant fiberglass fabric such as FR4/FR5 (epoxy resin and fiberglass fabric); epoxy resins such as bismaleimide triazine (BT) and cyanate ester (CE); epoxy resin laminates such as CEM1 or CEM3; polyimide dielectric (PD) materials, polytetrafluoroethylene (PTFE), carbon-hydrogen (CHn) polyimide films (e.g., Kapton™ films), polyester, or high-density interconnect (HDI) conductor boards to ensure the necessary flexural stability for protecting the connections to the hollow housing 3. To conserve weight and to provide a miniaturized design, however, the substrate material may also be made of rigid-flexible or flexible materials, for example in the form of printed conductor boards or films. However, in this case suitable reinforcements such as ribs provide the necessary stability of the connection housing 2.

Figure 4:
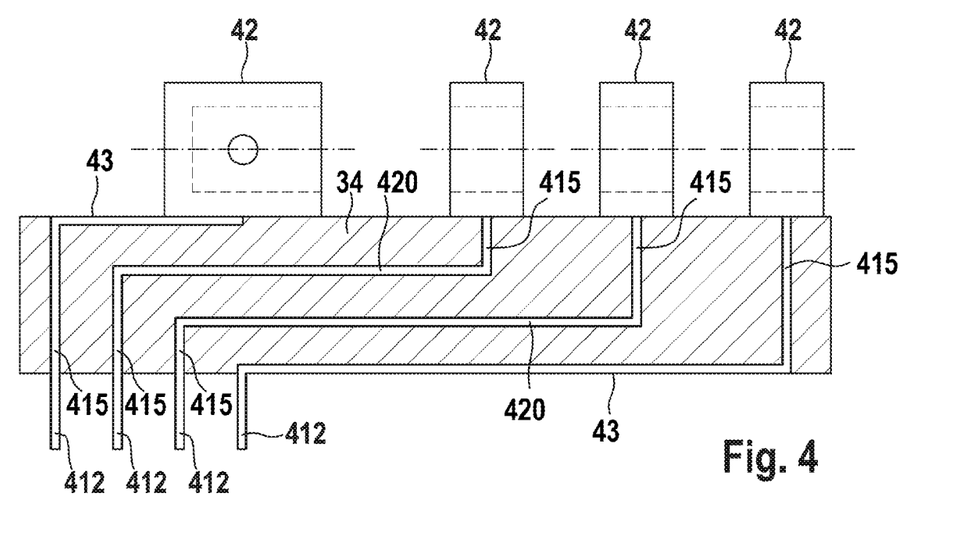
FIG. 4 shows a detailed sectional view of a multilayer substrate for the connection housing of a medical implant.

As shown in FIG. 4 in a sectional illustration of a multilayer substrate, as an alternative or additional embodiment of the connection housing 2 described immediately above, at strip conductor structures may be embedded in the substrate 34 in such a way that an embedded strip conductor structure 420 is surrounded by the substrate material. Passages (through-connections, vias, microvias, buried vias) 413 are provided in the substrate material to securely electrically connect the contacts 42 to the embedded strip conductor structures 420. This design as a multilayer substrate is provided primarily for bi- or multipolar connection housings, which have cavities and contact elements for more than one electrode line (for example, for cardiac resynchronization of all four cardiac chambers or for complex nerve or deep brain stimulation), or for complex plug-in connectors of the IS-4 standard as illustrated in FIG. 4.

Figure 5A:
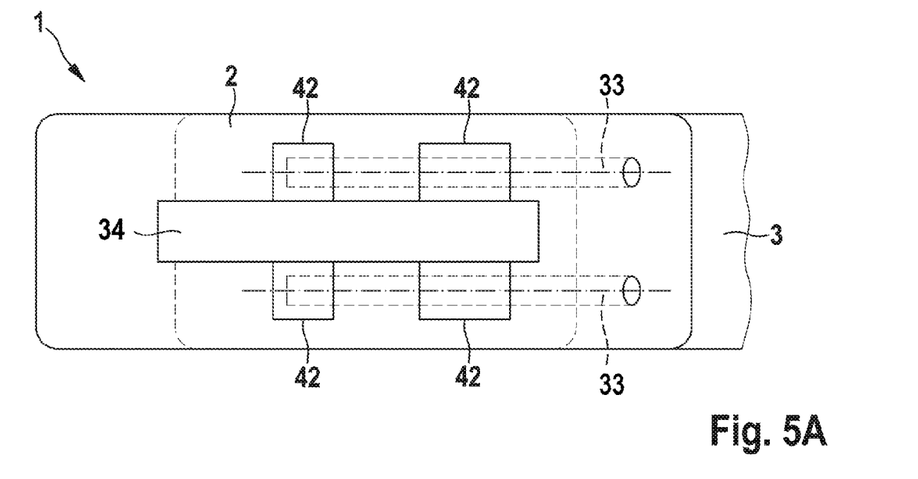
FIGS. 5A and 5B show a detailed view of a medical implant according to a third embodiment.
Figure 5B:
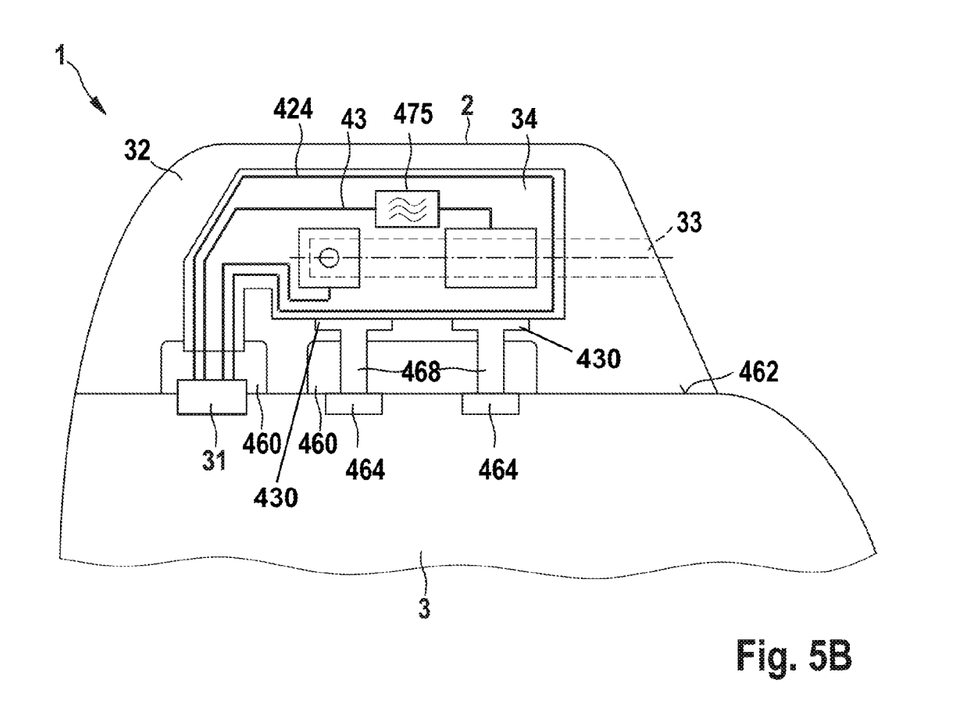

FIGS. 5A and 5B show top and side views, respectively, of medical implant 1 according to a further design in which it is possible to use strip conductor structures of the substrate 34 for purposes other than electrically connecting the circuit inside the hollow housing 3.

FIGS. 5A and 5B show a connection housing 2 for the medical implant 1 which is provided for bipolar stimulation. In a connection body 32 the connection housing includes two externally accessible cavities 33, into each of which a plug-in connector may be inserted at the proximal end of an electrode line, thus bringing the contacts 42 into electrical contact with the strip conductor structures 43, and thus with the circuit inside the hollow housing 3, via the pin for the feedthrough 31. For simplicity the two cavities 33 are adjacently situated. However, they may also be mounted one above the other relative to the location of the hollow housing 3. The cavities are situated on each side of the substrate 34. Also embedded in the connection body 32 is a printed conductor board substrate 34, made of insulating material, having at least one electrically conductive strip conductor structure 43. One or more contacts 42 are securely electrically connected to the substrate 34, and to one or more of the strip conductor structures 43 located in or on the substrate material of the substrate 34. The contacts 42 are securely electrically and mechanically connected to the substrate 34. The substrate 34 in turn is cast into the connection housing 2 in such a way that the contacts 42 are situated in the cavities 33 so that the electrode plug may be securely held within the cavities 33, whereas the remainder of the substrate 34 is surrounded by the insulating material of the connection housing 22. The substrate 34 also includes at least one strip conductor structure which is designed as an antenna structure 424. This antenna structure 424 has a first end and a second end which include laser welded, soldered, glued, or mounted connecting sites for a secure electrical and mechanical connection to the hollow housing 3. Each electrical connection is established by a pin for the housing feedthrough 31 of the hollow housing 3. The substrate 34 also has two anchors 430 which are provided for stabilizing the connection between the connection housing 2 and the hollow housing 3. The anchors 430 are either formed by the substrate material, thus forming a structure with the substrate 34, or are securely mechanically connected to the substrate by suitable means (e.g., laser welding, soldering, or gluing).

In each case the connection body 32 of the connection housing 2 surrounds the substrate 34 and at least one strip conductor structure 43, in at least some places, in such a way that the connecting sites at the second end 412 and the ends of the anchors 430 facing the hollow housing 3 are externally accessible to allow connection with the hollow housing 3. The connection body 32 accordingly has laterally accessible cavities 460 through which a connection may be established between the strip conductor structure and the feedthrough pin, and between the anchor and the hollow housing, using the joining process referenced above. However, according to one preferred design the substrate 34 and at least one strip conductor structure 43 are substantially enclosed by the connection body.

According to a further design, an additional passivation or insulation layer which is different from the connection body material may be applied directly to the substrate 34, forming an additional high-voltage insulating intermediate layer, for example, between the connection housing 2 and the substrate 34. This passivation or insulation layer may be composed of organic or inorganic materials and mixtures thereof (for example, ceramics or polymers).

For anchoring the anchor 430, the hollow housing 3 has a mounting surface 462 to which the connection housing 2 is securely joined. For this purpose the mounting surface 462 includes depressions 464 next to the feedthrough 31 which are suitable for accommodating the fasteners 468 preferably embodied as anchorings or anchors for the substrate 34, thereby positioning the connection housing 2 relative to the hollow housing 3 and fastening same.

Figure 6A:
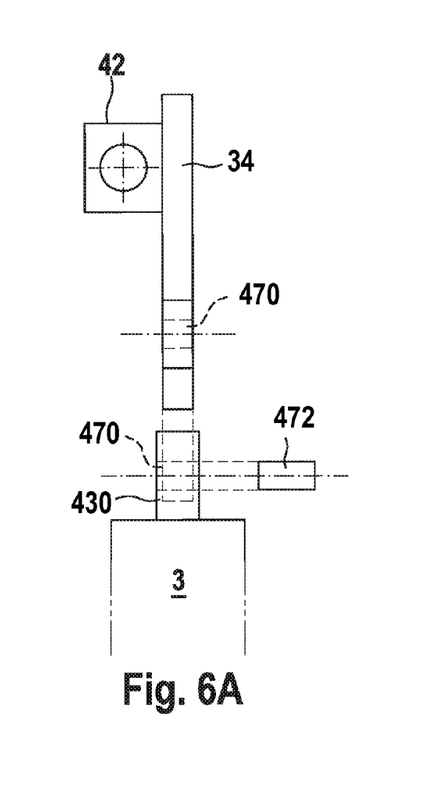
FIGS. 6A and 6B show a detailed view of a further possibility for anchoring the substrate to the hollow body.
Figure 6B:
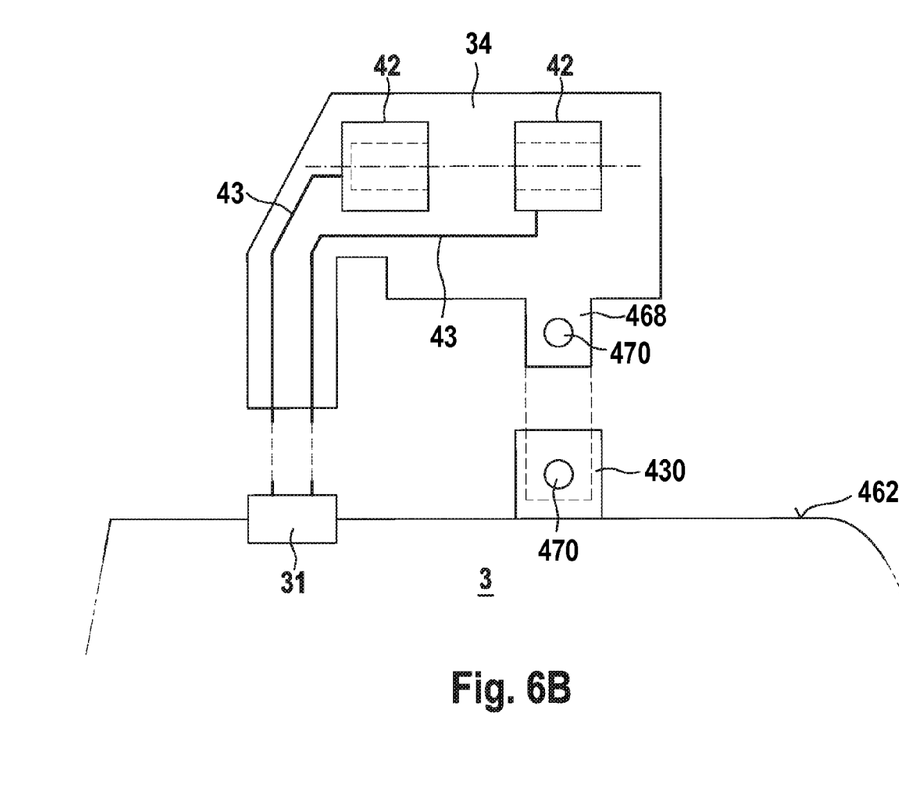

According to a further design of the anchoring with the hollow housing 3 illustrated in FIGS. 6A and 6B, one or more fasteners 468, for example protrusions, having boreholes or openings 470 may be present in the substrate 34 which are used for fastening, for example pinning, to the anchors 430 which are securely welded to the hollow housing 3. These protrusions of the fastener 468 are formed from the substrate material itself, and may have the shape of a projecting lug, for example. The anchors 430 are rigid anchors securely fastened to the mounting surface 462, with receptacles in the form of a recess which is accessible from one side from the direction opposite the hollow housing 3 and which is designed to accommodate the fasteners 468 for the substrate 34. The anchor 430 as well as the fastener 468 have perpendicularly situated boreholes or openings 470 through which a pin 472 may be guided for pinning. During manufacture the fasteners 468 for the substrate 34 are inserted into anchor receptacles from the direction opposite the hollow housing 3, and are pinned to the hollow housing 3 with or without a connection body 32. During extrusion coating or casting (vacuum casting or atmospheric casting) of the connection body 32 the anchoring may then be additionally stabilized using plastic or adhesive.

As further shown in FIG. 5B, a filter 475 may be provided on or in the substrate 34 which shields the circuit present in the hollow housing 3 from electromagnetic interference. The filter 475 may be a high-pass, low-pass, or band-pass filter, for example. Multiple filters may also be present. Illustrated as an example is a filter 475 on a strip conductor structure 43 between the contacts 42 and the electrical connection of the strip conductor structure 43 on the second end 412 to the feedthrough 31 in the hollow housing 3. The passive components on the substrate 34 which are necessary for the filter 475 may be easily assembled by automated means using SMD technology, for example. To conserve weight and to spare components and their assembly, the passive components may be integrated into the substrate 34 in multiple layers. Inductive resistors, coils, small capacitors, contacts, or cooling elements may be directly provided as a copper layer structure. Resistors may be pressed onto the surface or into the concealed layer of a multilayer substrate 34 using specialized pastes.

The substrate 34 may have one or more recesses at suitable locations for one or more radiopaque marker elements. These marker elements are electrically insulated in the recess, and contain information concerning the operating mode and the type of implant. The information becomes visible when the body is irradiated with X-rays. In addition, other identifying means may be present in or on the substrate 34, for example a radio frequency identification (RFID) transponder.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMBERS

1 Medical implant
2 Connection housing
3 Hollow housing
31 Glass/ceramic feedthrough
32 Connection body
33 Externally accessible cavity
34 Substrate
42 Contacts
43 Strip conductor structure
411 First ends of the strip conductor structure to which the contacts are electrically and mechanically connected
412 Second ends of the strip conductor structure at which an electrical and mechanical connection to the glass/ceramic feedthrough is present
414 Soldering lugs or pads on the substrate
415 Passage/via in the substrate
420 Embedded strip conductor structure
424 Antenna structure
430 Anchoring/anchor on the hollow housing
462 Mounting surface
464 Depressions for accommodating anchorings/anchors on the substrate
468 Fasteners
470 Borehole/opening in the anchoring on the hollow housing/the anchor on the substrate
472 Pin
475 Filter
460 Laterally accessible cavities

What is claimed is:

1. A connection housing for a medical implant, comprising:
    a connection body made of electrically insulating material which has an externally accessible cavity for connecting an implantable electrode line; and
    a substrate made of insulating material having an electrically conductive strip conductor structure, wherein a contact is securely electrically connected to the strip conductor structure present in or on the insulating material of the substrate such that the contact is also present in or on the insulating material of the substrate, and wherein the substrate is at least partly embedded in the connection body in such a way that the contact is present in the externally accessible cavity,
    wherein the substrate is designed as a printed circuit board, the insulating material of the substrate being selected from the group consisting of: fiber-reinforced plastics, ceramics, epoxy resins, epoxy resin laminates, resin-treated paper, epoxy fiberglass fabrics, polyimide films, polyester, and combinations thereof,
    wherein the contact includes plug-in connector receptacles or elastic sleeves.

2. The connection housing according to claim 1, wherein the strip conductor structure has a first end to which the contact is securely electrically connected, and a second end which includes connecting sites for a secure electrical connection to a hollow housing.

3. The connection housing according to claim 1, wherein the strip conductor structure is mounted on the substrate or is at least partly embedded in the substrate in such a way that a strip conductor surface facing away from the substrate is not covered by the substrate.

4. The connection housing according to claim 1, wherein the strip conductor structure is at least partly embedded in the substrate in such a way that the strip conductor is surrounded by the substrate, and passages are provided in the substrate to securely electrically connect the contacts to the strip conductor structure.

5. The connection housing according to claim 1, wherein the contacts are electrically connected to the strip conductor by welding, soldering, or gluing.

6. The connection housing according to claim 1, wherein one of a plurality of the strip conductor structures is designed as an antenna structure, and the antenna structure has a first and a second end which include the connecting sites for the secure electrical connection to the medical implant.

7. The connection housing according to claim 1, wherein the substrate has fasteners which are used for fastening the connection housing to the medical implant.

8. The connection housing according to claim 1, wherein the strip conductor structure is glued to the substrate.

9. The connection housing according to claim 1, wherein the strip conductor structure has a wire or ribbon shape and is made of a conducting material selected from the group consisting of copper, aluminum, gold, silver, stainless steel, titanium, niobium, tantalum, conductive adhesive, and conductive plastic.

10. The connection housing according to claim 1, wherein the substrate has recesses for a marker element which is electrically insulated in the recesses.

11. The connection housing according to claim 1, wherein the connection body surrounds the substrate and the strip conductor structure, at least in places, in such a way that connecting sites and anchors are externally accessible.

12. The connection housing according to claim 11, wherein the substrate and the strip conductor structure are surrounded by the connection body.

13. A connection housing for a medical implant, comprising:
    a connection body made of electrically insulating material which has an externally accessible cavity for connecting an implantable electrode line, the connection body attached to a hollow housing of the medical implant, the hollow housing configured for housing a control electronics system of the medical implant; and a substrate disposed in the connection body and made of insulating material having an electrically conductive strip conductor structure, wherein a contact is securely electrically connected to the strip conductor structure present in or on the insulating material of the substrate such that the contact is also present in or on the insulating material of the substrate, and wherein the substrate is at least partly embedded in the connection body in such a way that the contact is present in the externally accessible cavity, wherein the substrate is designed as a printed circuit board for connecting the contact with the control electronics system in the hollow housing, the insulating material of the substrate being selected from the group consisting of: fiber-reinforced plastics, ceramics, epoxy resins, epoxy resin laminates, resin-treated paper, epoxy fiberglass fabrics, polyimide films, polyester, and combinations thereof, wherein the contact includes plug-in connector receptacles or elastic sleeves.

* * * * *